(12) United States Patent
Burnham et al.

(10) Patent No.: US 8,673,184 B2
(45) Date of Patent: Mar. 18, 2014

(54) SYSTEMS AND METHODS FOR PROVIDING OVERCHARGE PROTECTION IN CAPACITIVE COUPLED BIOMEDICAL ELECTRODES

(75) Inventors: Kenneth Burnham, Warren, MA (US); Richard Skov, Spencer, MA (US); Stephen Tomas, Sturbridge, MA (US)

(73) Assignee: FLEXcon Company, Inc., Spencer, MA (US)

( * ) Notice: Subject to any disclaimer, the term of this patent is extended or adjusted under 35 U.S.C. 154(b) by 267 days.

(21) Appl. No.: 13/272,545

(22) Filed: Oct. 13, 2011

(65) Prior Publication Data

US 2013/0092882 A1   Apr. 18, 2013

(51) Int. Cl.
*H01B 1/24* (2006.01)
*H01B 3/00* (2006.01)
*A61B 5/0408* (2006.01)

(52) U.S. Cl.
USPC .......................................... 252/511; 607/115

(58) Field of Classification Search
None
See application file for complete search history.

(56) References Cited

U.S. PATENT DOCUMENTS

| | | | |
|---|---|---|---|
| 4,188,449 A | | 2/1980 | Lu et al. |
| 4,367,745 A | * | 1/1983 | Welage ............................ 606/32 |
| 4,417,174 A | | 11/1983 | Kamijo et al. |
| 4,588,762 A | * | 5/1986 | Mruk et al. ...................... 524/45 |
| 4,687,968 A | | 8/1987 | Frayer |
| 4,816,717 A | | 3/1989 | Harper et al. |
| 4,852,571 A | | 8/1989 | Gadsby et al. |
| 5,082,595 A | | 1/1992 | Glackin |
| 5,321,069 A | | 6/1994 | Owens |
| 5,409,777 A | | 4/1995 | Kennedy et al. |
| 5,479,070 A | | 12/1995 | Murakami |
| 5,552,679 A | | 9/1996 | Murasko |
| 5,800,685 A | | 9/1998 | Perrault |
| 5,821,691 A | | 10/1998 | Richie et al. |
| 5,906,720 A | | 5/1999 | Ferguson et al. |
| 6,121,508 A | | 9/2000 | Bischof et al. |
| 6,198,216 B1 | | 3/2001 | Kosa et al. |
| 6,207,077 B1 | | 3/2001 | Burnell-Jones |
| 6,327,487 B1 | * | 12/2001 | Stratbucker ................. 600/382 |
| 6,432,516 B1 | | 8/2002 | Terashima et al. |
| 7,620,439 B2 | * | 11/2009 | Menon et al. ................. 600/391 |

(Continued)

FOREIGN PATENT DOCUMENTS

| | | |
|---|---|---|
| JP | 2257590 | 6/1990 |
| JP | 7011247 | 1/1995 |

(Continued)

OTHER PUBLICATIONS

Solid surface energy data (SFE) for common polymers, www.surface-tension.de/solid-surface-energy.htm, retrieved Sep. 1, 2010, 2 pages.

(Continued)

*Primary Examiner* — Mark Kopec
(74) *Attorney, Agent, or Firm* — Gesmer Updegrove LLP

(57) ABSTRACT

An alternating electric field responsive biomedical composite is disclosed that provides capacitive coupling through the composite. The biomedical composite includes a binder material, a polar material that is substantially dispersed within the binder material, and electrically conductive particles within the binder material. The polar material is responsive to the presence of an alternating electric field, and the electrically conductive particles are not of sufficient concentration to form a conductive network through the composite unless and until the composite becomes overcharged.

19 Claims, 14 Drawing Sheets

(56) References Cited

U.S. PATENT DOCUMENTS

| | | | |
|---|---|---|---|
| 7,651,638 B2 * | 1/2010 | Segall et al. | 252/511 |
| 7,998,574 B2 * | 8/2011 | Segall et al. | 428/355 AC |
| 8,273,268 B2 * | 9/2012 | Huang et al. | 252/511 |
| 2001/0038925 A1 | 11/2001 | Barton et al. | |
| 2009/0005667 A1 | 1/2009 | Cui et al. | |
| 2010/0016702 A1 | 1/2010 | Greene et al. | |
| 2012/0145315 A1 | 6/2012 | Knaapila et al. | |
| 2013/0092881 A1 * | 4/2013 | Burnham et al. | 252/511 |

FOREIGN PATENT DOCUMENTS

| | | |
|---|---|---|
| JP | 2000260561 | 9/2000 |
| WO | 0029493 | 5/2000 |
| WO | 0174119 | 10/2001 |
| WO | 0219020 | 3/2002 |
| WO | 2010151141 A1 | 12/2010 |
| WO | 2010151142 A1 | 12/2010 |
| WO | 2010151148 A1 | 12/2010 |
| WO | 2012076612 A1 | 6/2012 |
| WO | 2012081991 A1 | 6/2012 |
| WO | 2012081992 A2 | 6/2012 |
| WO | 2012085084 A3 | 6/2012 |
| WO | 2012085105 A1 | 6/2012 |

OTHER PUBLICATIONS

International Search Report and Written Opinion issued on Apr. 3, 2013 in connection with International Application PCT/US2012/059654, 11 pages.

* cited by examiner

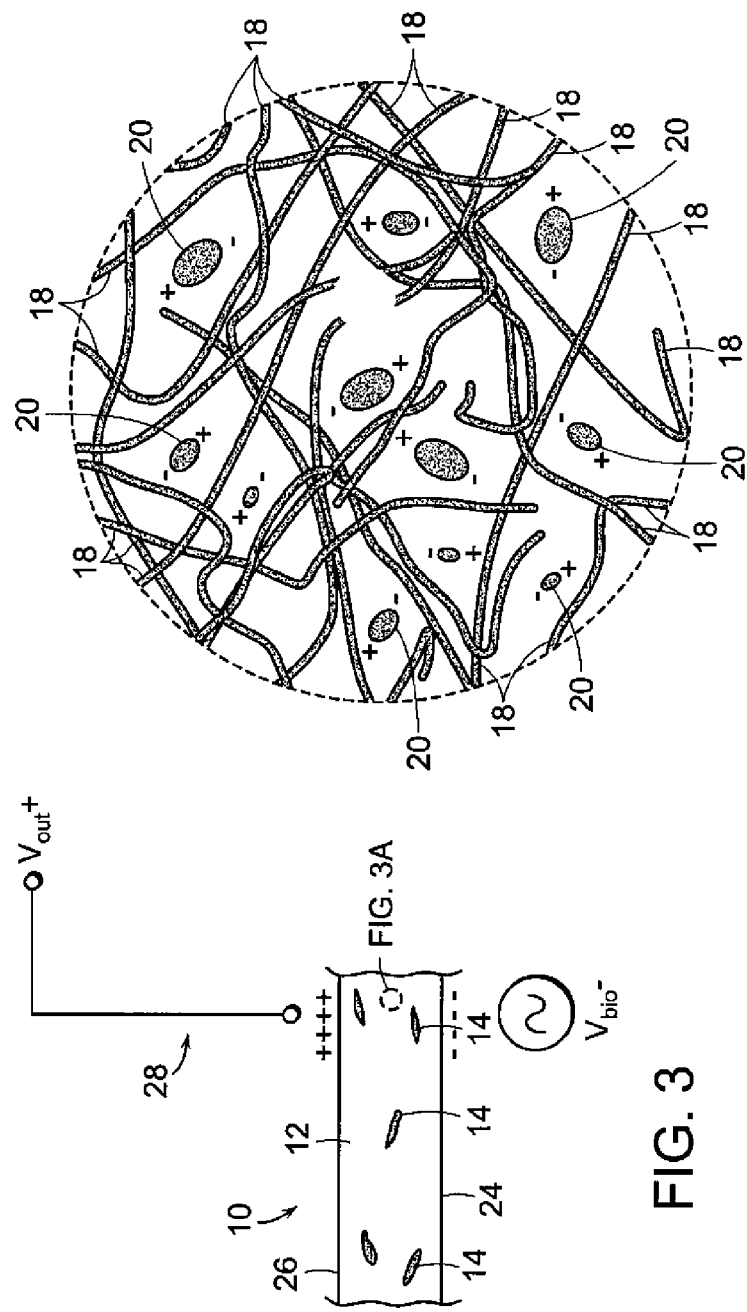

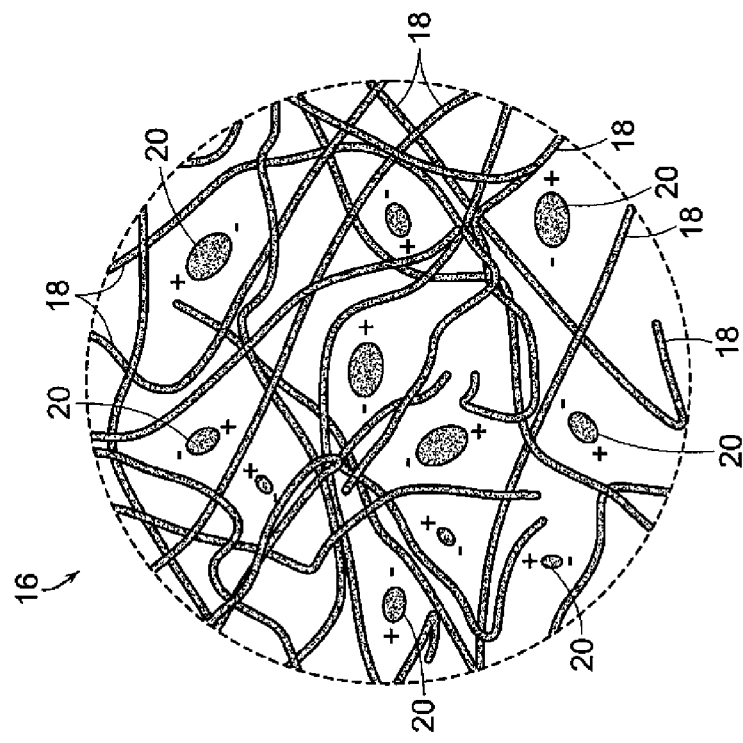
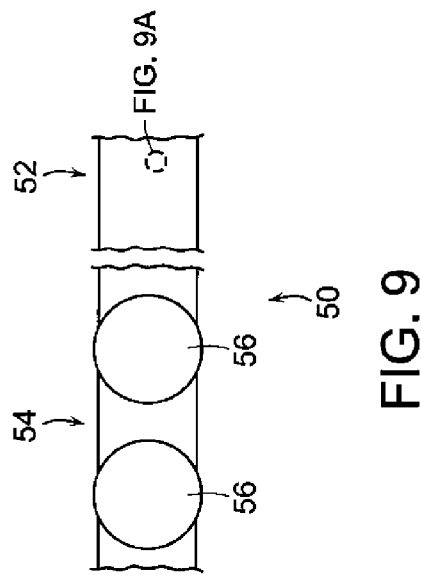
FIG. 9A
FIG. 9

SYSTEMS AND METHODS FOR PROVIDING OVERCHARGE PROTECTION IN CAPACITIVE COUPLED BIOMEDICAL ELECTRODES

BACKGROUND

The invention generally relates to conductive and non-conductive materials that are used in conjunction with providing an electric field at one side of such a material responsive to an electric field on the other side of the material for biomedical applications.

The design of an electrically conductive pressure sensitive adhesive (PSA) for biomedical applications has long presented challenges at least because adhesive strength and flexibility generally decrease with increased electrical conductivity. The materials that are typically used (e.g., added) to provide good electrical conductivity are generally less flexible and inhibit adhesion. A conventional way to prepare a conductive coating is to fill a polymeric material with conductive particles, e.g., graphite, silver, copper, etc., then coat, dry and cure the polymeric binder. In these cases, the conductive particles are in such a concentration that there is a conductive network formed when the particles are each in physical contact with at least one other neighboring particle. In this way, a conductive path is provided through the composite.

For pressure sensitive adhesives (PSAs), however, if the particle concentration is high enough to form a network in which particle-to-particle contact is maintained then there is little chance that the polymer (e.g., elastomer) system of the PSA component is present in high enough concentrations to flow out to make surface-to-surface contact between the substrates and an electrode, i.e., act as an adhesive. Conversely, if the PSA component is in sufficient concentration to make sufficient surface contact to the substrate, it would have to interrupt adjacent conductive particles such that particle-to-particle contact is disrupted.

Another type of electrically conductive PSA includes conductive spherical particles with diameters equal to or greater than the thickness of the PSA. In this fashion the signal or current may be carried along the surface of the particles, thus providing current flow anisotropically in the z dimension of the adhesive. Such a composite has not been shown in the prior art to be usable for a biomedical adhesive.

Salts, such as sodium or potassium chloride, readily dissolve when in an aqueous medium, and their ions dissociate (separate into positive and negative ions). The dissociated ions may then convey an electrical current or signal. For this reason, salts have long been added to water, which then may be added to polymeric and elastomeric materials, to provide good electrical conductivity. For example, U.S. Pat. No. 6,121,508 discloses a pressure sensitive adhesive hydrogel for use in a biomedical electrode. The gel material is disclosed to include at least water, potassium chloride and polyethylene glycol, and is disclosed to be electrically conductive. U.S. Pat. No. 5,800,685 also discloses an electrically conductive adhesive hydrogel that includes water, salt, an initiator or catalyst and a cross linking agent. The use of such hydrogels however, also generally requires the use of a conductive surface at one side of the hydrogel (away from the patient) that is capable of receiving the ionicly conductive charge, such as silver/silver chloride, which is relatively expensive.

While these hydrogel/adhesives can have good electrically conductive properties, they often have only fair adhesion properties. Another downside is that the electrical conductivity changes with changing water content, such as changes caused by evaporation, requiring that the hydrogels be maintained in a sealed environment prior to use, and then used for a limited period of time due to evaporation.

U.S. Pat. No. 7,651,638 discloses a water insensitive alternating current responsive composite that includes a polymeric material and a polar material (such as a salt) that is substantially dispersed within the polymeric material. The polar material however, is not employed to provide electrical conductivity via ionic conduction. The polymeric material and the polar material are chosen such that the two materials each exhibit a mutual attraction that is substantially the same as the attraction within the individual materials. Because of this, the polar material neither clumps together nor blooms to a surface of the polymeric material, but remains suspended within the polymeric material. This is in contrast to the use of these salts in other applications that are intended to bloom to a surface to provide a conductive layer along a surface, e.g., for static discharge.

The composites of U.S. Pat. No. 7,651,638, however, remain dielectrics and have high resistance, and are therefore not suitable for use in certain applications, such as providing electrical stimulus to a human subject (defibrillation and/or transcutaneous electrical nerve stimulations, etc.) due to the high resistance of the material. This type of signal detecting adhesive is also not capable of dissipating the charge overload in a timely enough fashion as per AAMI EC12-2000-4.2.2.4, which is directed to defibrillation overload recovery (DOR). The materials are therefore not suitable for use as a monitoring electrode through which a signal may be needed to be detected after a defibrillation charge is applied to a patient. The failure to pass AAMI EC12-2000-4.2.2.4 is due to the high impedance of these capacitively coupled adhesives.

There remains a need, therefore, for a composite for use in conducting a representative signal and/or current through at least the z dimension of a PSA in a biomedical electrode, such that the use of conductive particles may be minimized, while preserving the adhesive's properties, so that both good electrical performance and good adhesive properties may be maintained.

SUMMARY

The invention provides an alternating electric field responsive composite for use in a biomedical electrode that provides capacitive coupling through the composite in accordance with an embodiment. The composite includes a binder material, a polar material that is substantially dispersed within the binder material, and electrically conductive particles within the binder material. The polar material is responsive to the presence of an alternating electric field, and the electrically conductive particles are not of sufficient concentration to form a conductive network through the composite, yet will provide an overcharge protection in the event, for example, of a defibrillation procedure.

In accordance with an embodiment, the overcharge protection is provided by having the electrically conductive particles migrate via electrophoresis to form electrically conductive paths through the composite.

In accordance with another embodiment, the binder material and the polar material exhibit mutual molecular compatibility, and the electrically conductive particles remain substantially isolated from one another within the binder material.

In accordance with a further embodiment, the electrically conductive particles may be carbon or graphite in the form of powder, flakes granules, nanotubes, etc.

In accordance with a further embodiment, the invention provides a method of providing overcharge protection in a biomedical electrode using electrophoresis.

BRIEF DESCRIPTION OF THE DRAWINGS

The following description may be further understood with reference to the accompanying drawings in which:

FIG. 3 shows an illustrative diagrammatic view of the composite of FIG. 1 in the presence of a falling biomedical electric field ($V_{bio-}$), and FIG. 3A shows an enlarged view of a portion thereof;

FIG. 9 shows an illustrative diagrammatic view of a composite in accordance with a further embodiment of the invention, and FIG. 9A shows an enlarged view of a portion thereof;

Figure 1A:
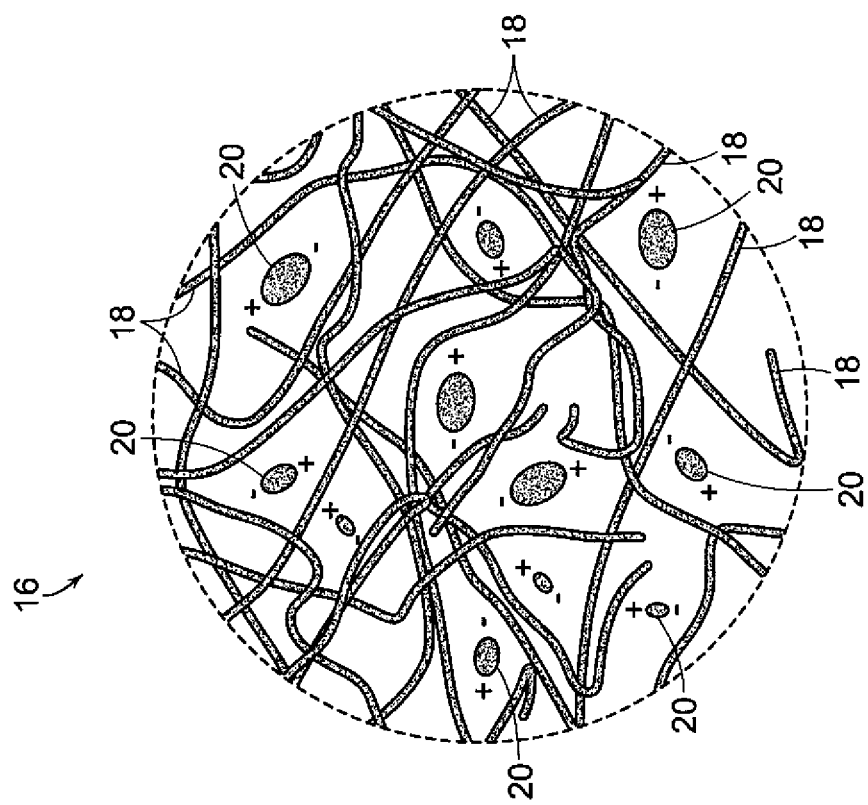
FIG. 1A shows an enlarged view of a portion thereof.

The drawings are shown for illustrative purposes only and are not to scale.

DETAILED DESCRIPTION

Applicants have discovered that although the composites of U.S. Pat. No. 7,651,638 are disclosed to function by capacitive coupling, conductive particles may be added to such composites with surprising results; although they are not added in such quantity that they form a conductive network, the electrically conductive composites undergo electrophoresis when the composite is exposed to an overcharge voltage such as, for example, the 200 volts DC as used in AAMI EC12-2000-4.2.2.2.4. Such an overvoltage charge would occur if a defibrillation procedure was performed on a patient being monitored. Failure to dissipate the charge from the electrode in a timely enough fashion so that the electrodes can again pickup ECG signals, may result in additional defibrillation procedures being done due to the absence of an ECG signal. Further, a capacitive discharge from the electrode to the patient may cause burns to the patient's skin.

It has been found however, that the electrically conductive particles, when in the presence of the overcharge voltage, migrate within the binder so as to form independent conductive paths through the composite, thereby causing the resistivity through the composite to drop significantly. This functionality provides an overcharge protection to the biomedical electrode.

The impedance may be measured by the method described in AAMI EC12-2000-4.2.2.1 (AC Impedance), which provides a maximum of 3000 Ohms permitted for any single value and an average not to exceed 2000 Ohms. The AC impedance method used herein was modified to 20 Hz rather than 10 Hz, using a QuadTech 1920 Precision LCR meter sold by QuadTech, Inc. of Marlborough, Mass.

It has been found however, that examples of composites of the invention including just 5% by weight carbon particles have resistances of less than 1000 Ohms following overcharging, meaning that the composites pass AAMI EC12-2000-4.2.2.4, yet function by the capacitive coupling techniques disclosed in U.S. Pat. No. 7,651,638 before being subjected to an overcharge electric field. It has further been found, in fact, that by adding as little as (1%) of a conductive particle either randomly dispersed or position specific within a polymeric material including a polar material as described above, composites may be formed that pass AAMI EC12-2000-4.2.2.1 and AAMI EC12-2000-4.2.2.4 following overcharging. Lower resistance mixtures (following overcharging) were obtained using a 2.5% conductive particle addition, and still lower resistance mixtures (following overcharging) were obtained using a 5% conductive particle addition.

A further aspect of the present invention is that since the representative signal from the aligning/relaxing electric fields of the polar material is present in the z direction, a large area (in the x and y directions) material may be employed that contains multiple receiver contacts on the common large area material. The material, therefore, is anisotropic in that sensor contacts may be adjacent one another on the common composite material without cross signal detection. Moreover, the composite material remains anisotropic following overcharging since the conductive paths formed by electrophoresis are discrete from one another as discussed further below.

The requirements for the binder material (e.g., polymeric material or elastomeric material), the polar material and the conductive material are that the materials interact in such a way that neither the polar material nor the conductive material clumps together within the binder material or blooms to a surface of the binder material. If the conductive material has a surface energy similar to that of the binder material, then it will remain suspended within the binder material yet not be in sufficient concentrations to provide electrical conductivity through the material prior to any overcharging.

Figure 1:
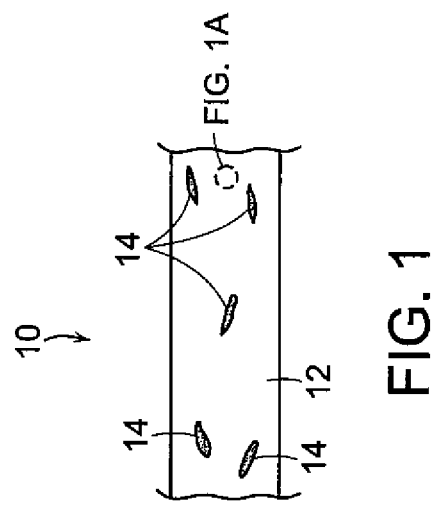
FIG. 1 shows an illustrative diagrammatic view of a composite in accordance with an embodiment of the invention prior to electrophoresis.

FIG. 1 for example, shows a composite 10 in accordance with an embodiment of the invention that includes a binder material 12 and conductive particles 14 dispersed within the binder material 12. As shown at the diagrammatic enlarged view 16 in FIG. 1A, the binder material 12 includes a polymeric material 18 and a polar material 20 that are combined at a molecular scale. This may be achieved, for example, by introducing the polar material (while in an evaporative water/alcohol solution) into the solvated and/or liquid dispersed polymeric material and then permitting the water/alcohol solution to evaporate leaving the polar material within the polymeric material.

In accordance with an embodiment of the invention, the polymeric material may, for example, be an acrylic adhesive such as may be represented as

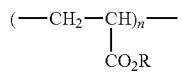

where R may vary and may be any of an ethyl, or a butyl or a 2-ethylhexyl or other organic moiety, and n is a number of repeating units. For example, the polymeric material may be a FLEXcon V95 pressure sensitive adhesive as sold by FLEXcon Company, Inc. of Spencer, Mass.

In an embodiment, the polar material may be a quaternary ammonium salt such as may be represented as:

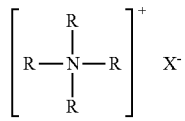

where R=H or some carbon based moiety, and where any of the R groups may be the same or different. For example, the polar material may be an Arquad HTL8-MS quaternary ammonium salt sold by Akzo Nobel Surfactants of Chicago, Ill.

An objective of the selection of the combination of the binder material and the polar material is that the two materials each exhibit a mutual attraction that is very similar to the attraction that each material has to its own molecules. This results in the polar material being homogeneously dispersed within the binder material. The suitability of the combination of the polymeric material and the polar material may be identified by the following procedure. First, a polar material is combined with the polymeric material in about five different concentrations (typically between about 5% to about 45% by weight). Then the adhesive and salt composite is drawn onto a release liner (of about 1.5 mil), and permitted to dry and cure. The surface of the composite is then inspected after a short period of time. If the polar material has crystallized out or bloomed to the surface, then the combination of components is not compatible. If, on the other hand, the composite is clear, it is subjected to the next level of compatibility testing. The samples should then be subjected an exposure test in which the samples are exposed to 100 F with 95% relative humidity for 3 days. The samples are then again inspected to determine whether the polar material has migrated toward either surface. If there has been no migration of the polar material and the composite is clear, then the dielectric constant for the composite is determined and the composite is tested for use as a medical monitoring material.

With reference again to the diagrammatic enlarged view 16 of FIG. 1, the binder material and the polar material are selected to be compatible but not such that they undergo an ionic disassociation change such as would occur, for example with NaCl in water. The molecule-scale polar material 20 is therefore dispersed within the binder material 18 but given the molecular weight of the polar material and the non-protic medium of the adhesive, little or none true ionic disassociation would be expected.

Figure 2A:
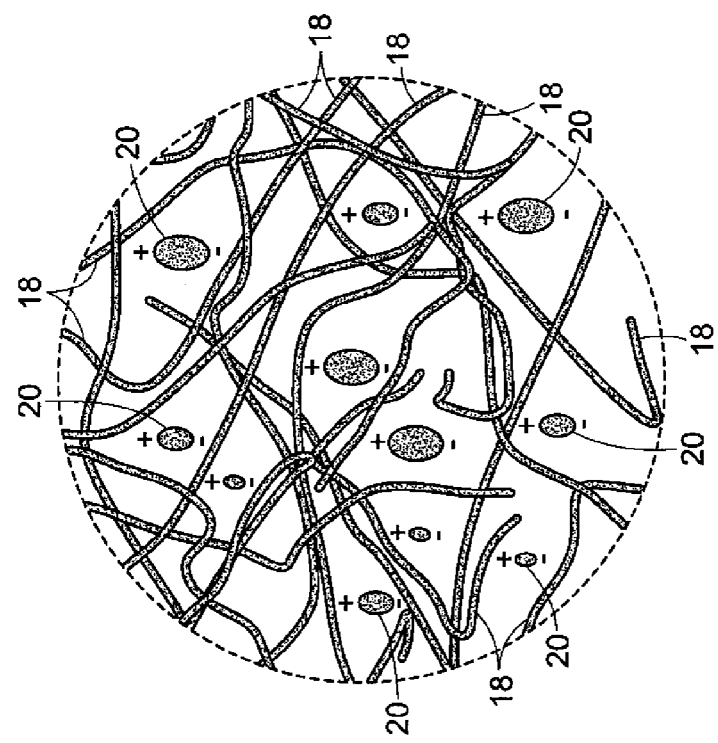
FIG. 2A shows an enlarged view of a portion thereof.
Figure 2:
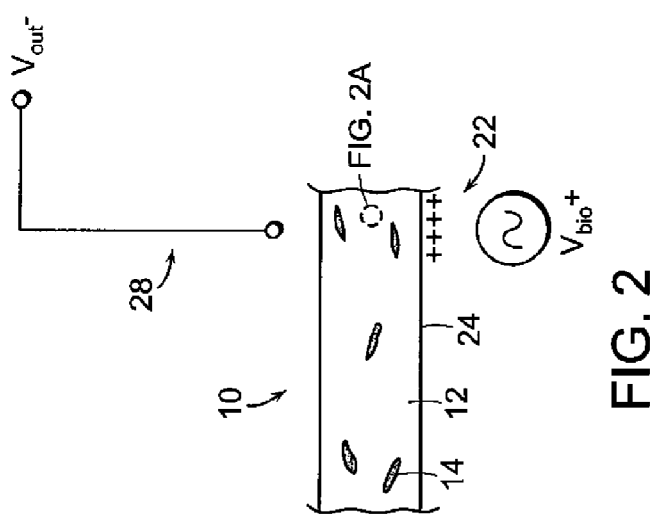
FIG. 2 shows an illustrative diagrammatic view of the composite of FIG. 1 in the presence of a rising biomedical electric field ($V_{bio+}$)

As shown in FIG. 2, when an external positive bio-electric field ($V_{bio+}$ as generally shown at 22) is present at one side 24 of the composite 10, as shown in the enlarged view of FIG. 2A, the polar material 20 responds by aligning with the external positive electric field as shown in the enlarged view. As shown in FIG. 3, when the external bio-electric field decreases ($V_{bio-}$) at the one side 24 of the composite 10, as shown in the enlarged view of FIG. 3A, the polar material 20 is free to migrate to random orientations. When this occurs, a positive charge ($V_{out}+$) is provided at a second opposite surface 26 of the composite 10. Upon the bio-electric field collapsing, the polar material under normal thermal motion, returns to a random state. The released electrical potential may be detected by an electrode as shown at 28. As the bio-electric field alternates therefore from $V_{bio-}$ to $V_{bio+}$ to $V_{bi-}$ etc., the output signal provides a representative alternating signal of $V_{out+}$ to $V_{out-}$ to $V_{out+}$ etc.

The voltage at the electrode on the surface 26, therefore, alternates in the presence of an alternating electric field at the opposite surface 24. In this way, an alternating electric field from the first side of the composite may be represented by a second alternating electric field provided at the electrode 28. Note that the capacitance may vary depending upon the size (e.g., the X-Y plane and the total distance between conductive surfaces.

The conductive particles should have a surface energy that is at least slightly greater than that of the binder material to ensure that the binder material sufficiently wets the surface of the conductive particles. The density and surface area of the conductivity of the particles 14 are important considerations. Applicants have found, for example, that carbon (e.g., graphite powder, flakes, granules or nanotubes etc.) having densities in the range of, for example, about 0.35 g/cm$^3$ to about 1.20 g/cm$^3$, and preferably between about 0.5 g/cm$^3$ to 1.0 g/cm$^3$, are suitable for use as the conductive material. The surface energy of the graphite is, again, preferably higher than that of the binder to ensure sufficient wetting of the surfaces of the particles 14. In the above example, the graphite particles have a specific surface energy of 55 dynes/cm and the binder disclosed above has a surface energy of less than 40 dynes/cm.

Figure 4A:
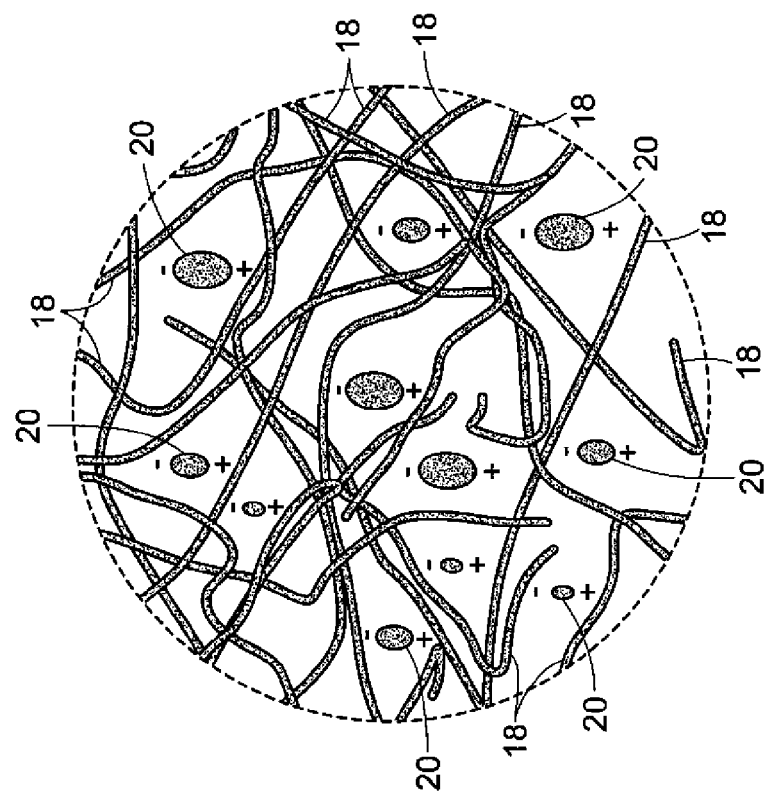
FIG. 4A shows an enlarged view of a portion thereof.
Figure 4:
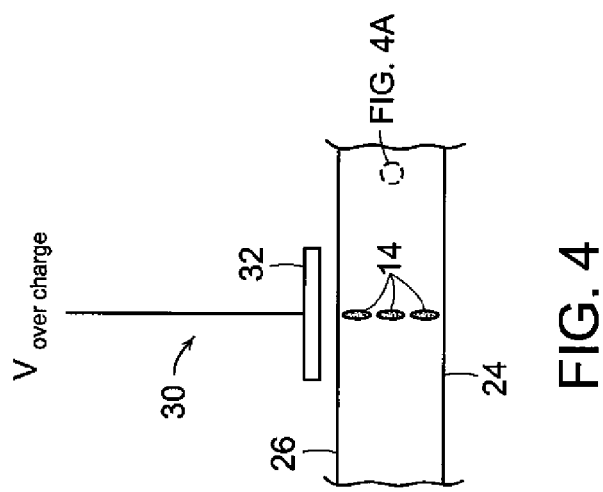
FIG. 4 shows an illustrative diagrammatic view of the composite of FIG. 1 in the presence of an overcharge electric field ($V_{overcharge}$)

FIG. 4 shows the composite of FIG. 1 in the presence of an overvoltage charge 30 ($V_{overvoltage}$). As shown, in the presence of such an overvoltage charge 30 on an electrode 32, as shown in the enlarged view of FIG. 4A, the conductive particles 14 align with the shortest distance between a high charge and a low charge (such as ground) due to an electrophoresis process. The aligned conductive particles thereby migrate to form a permanent conductive path through the composite as shown. The overvoltage charge may now conduct along the path formed by the conductive particles 14.

Figure 5A:
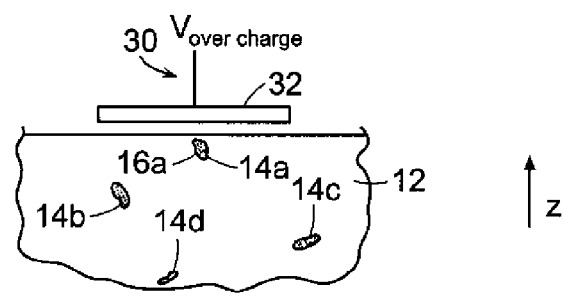
FIGS. 5A-5C show illustrative diagrammatic views of the composite of FIG. 1 at successive moments after a direct current (DC) overcharge electric field is applied showing the electrophoresis activity.
Figure 5B:
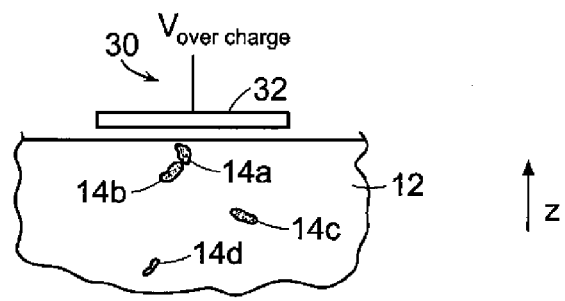
Figure 5C:
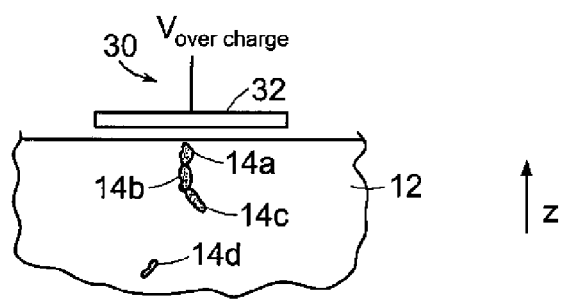

In particular, FIGS. 5A-5C show the electrophoresis process that occurs upon overcharging in more detail. As shown in FIG. 5A, when a large voltage potential is applied, e.g., 5, 10, 50, 100 or 200 volts or higher AC or DC, a particle 14a that is near the surface aligns in the z-direction. Once this occurs, the inner end 16a of the particle 14a is now closer to the opposing surface, causing the charge on the inner end 16a to be slightly higher than the charge on the surrounding inner surface of the composite. This causes another nearby particle 14b to be attracted to the inner end 16a of the particle 14a as shown in FIG. 5B. The inner end of the particle 14b is now highly charged, causing nearby particle 14c to be attracted to it as shown in FIG. 5C. Further particles (e.g., 14d as shown) are further attracted to the ends of the thus formed path. This all occurs rapidly and the attractive/aligning force causing the electrophoresis is believed to become stronger as the path is formed as the distance between a first electrode and the growing agglomerate attached to the other electrode gets smaller.

Figure 6A:
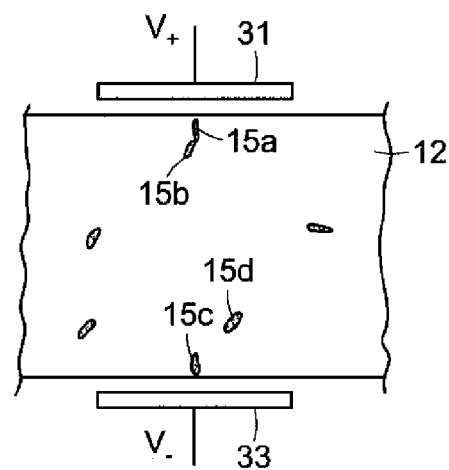
FIGS. 6A-6B show illustrative diagrammatic views of the composite of FIG. 1 at successive moments after an alternating current (AC) overcharge electric field is applied showing the electrophoresis activity.
Figure 6B:
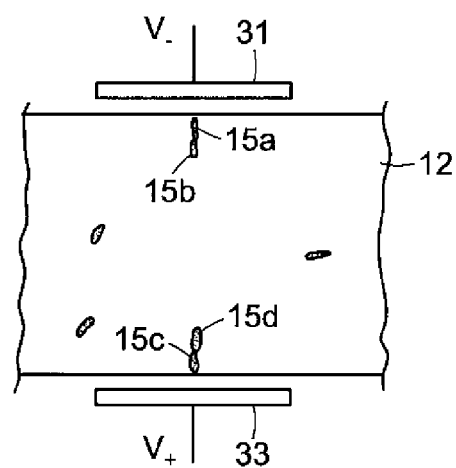

As shown in FIG. 6A, when an AC overvoltage field is applied (again, e.g., 5, 10, 50, 100 or 200 volts or higher), the particles 15a and 15b form along a first side of the composite 12 that has a positive voltage applied to it at a first conductor 31. When a positive voltage charge is then applied at the opposite conductor 33, the conductive particles 15c and 15d then begin to agglomerate from the lower side of the composite as shown in FIG. 6B. By thus alternating the agglomeration process between opposite sides, the AC overvoltage causes a path to be formed that essentially meets in the middle.

Regardless of whether the overvoltage charge is DC or AC, the higher the voltage, the faster the particles align, but with a relatively low voltage (e.g., about 5 volts or higher), the particles align more slowly, but do still eventually align.

Figure 7:
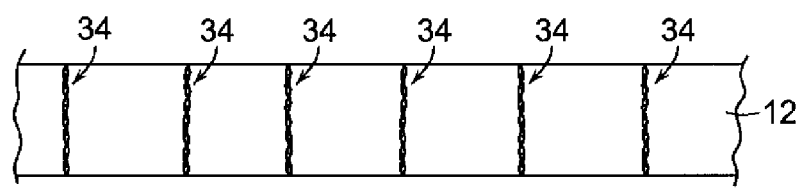
FIG. 7 shows an illustrative diagrammatic view of a composite of the present invention following application of an overcharge electric field over a common overcharge area.
Figure 8:
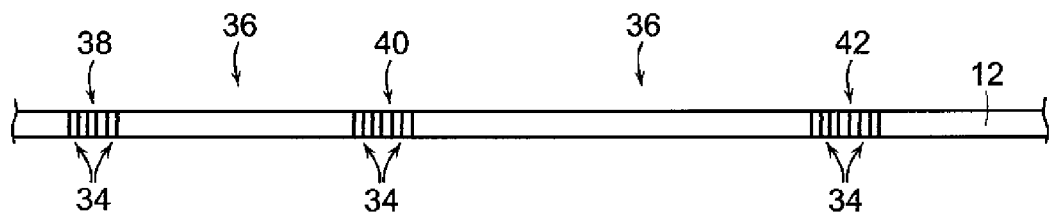
FIG. 8 shows an illustrative diagrammatic view of a wide area of a composite of the present invention showing the selectively anisotropic nature of the composites of the invention providing the multiple discontinuous overcharge areas may be formed.

As shown in FIG. 7, following overcharging over a small area of the composite, multiple conductive paths 34 may be formed through the composite, wherein each conductive path is formed by aligned conductive particles. As shown in FIG. 8, groups of such conductive paths 38, 40, 42 may be separated from one another through selective application of overcharging fields, permitting selected areas of the composite to be electrically conductive, while other areas 36 of the composite exhibit a high dielectric constant and are therefore not electrically conductive.

In accordance with a further embodiment, a composite 50 of the invention may include a first portion 52 that exhibits capacitive coupling as described above, while another portion 54 of the composite includes conductive paths, e.g., formed of spheres 56 of carbon, that extend just slightly through the binder material as shown in FIG. 9 as well as the enlarged view thereof of FIG. 9A. Such as composite may be used to selectively provide capacitive coupling in one area 52 (as discussed above with reference to FIGS. 1-3) and/or to provide electrical conductivity in a different area 54.

In accordance with an embodiment, in one example, a polar material (Arquad HTL-8 (AkzoNobel), 20% by weight on solids) was added to a liquid sample of FLEXcon's V-95 acrylic PSA. To this, 5% by weight (solids of the V-95 FLEXcon and Arquad blend) of a carbon particle (the Aquablack 5909 carbon particles from Solution Dispersions Inc., Cynthiana Ky.), was uniformly dispersed. This mixture was coated onto a 2 mil (50 micron) siliconized one side PET film, dried and cured for 10 min in a 160° F. vented laboratory oven, to a dried deposition of 2 mil (50 micron).

It has been found that after performing the test procedure in AAMI E12-2000-4.2.2.4 the adhesive composite with the conductive particles dispersed within undergoes a change. Post device overload recovery (DOR) tested materials will now pass AAMI E12-2000-4.2.2.1. It has also been found that like the capacitively coupled binder material, which has Z dimension signal receptivity, the post DOR material maintains this Z dimension signal receptivity. In addition the conductive particle variant, post DOR test, material also conveys current in the Z dimension. Interestingly this maintenance of Z dimensionality allows this adhesive to be used in applications as disclosed in U.S. Patent Application Publication No. 2010-0036230 which teaches the formation of a bio-sensor array fashioned with one continuous layer of adhesive, the disclosure of which is hereby incorporated by reference in its entirety.

Composites in accordance with certain embodiments of the present invention, begin with substantially separated particles uniformly dispersed within the adhesive, then requires a second step, i.e., applying an electric field to form the conductive structures. This is a decided advantage as it allows for the placement of conductive structures, i.e., in the Z dimension and if needed, place the Z dimensioned structures at specific X,Y, locations thus allowing for a specific point to point electrical contact.

The following Examples demonstrate the effect of the conductive particle addition to the binder material discussed above.

Example 1

To a liquid sample of FLEXcon's V-95 acrylic PSA, is added the polar material, Arquad HTL-8 (AkzoNobel), 20% by weight on solids, to this 5% by weight (solids of the V-95 and Arquad blend) of a carbon particle (Aquablack 5909 from Solution Dispersions Inc., Cynthiana Ky.), was uniformly dispersed and designated as Sample 1. This mixture was coated on a 2 mil (50 micron) siliconized one side PET film, dried and cured for 10 min in a 160° F. vented laboratory oven, to a dried deposition of 2 mil (50 micron).

Also prepared at this time was the composite of just the V-95 acrylic adhesive and the Arquad (20% by solids weight), no carbon, as per the teachings in U.S. Pat. No. 7,651,638. This mixture was also 2 mil (50 microns) siliconized one side PET film, dried and cured for 10 min in a 160° F. vented laboratory oven, to a dried deposition of 2 mil (50 microns) and was designated as Sample 2.

Similarly a third sample was prepared consisting of only V-95 arcylic adhesive and 5% carbon, with no polar material (Arquad). The sample was processed in the same manner as for samples 1 and 2, and this sample was designated as Sample 3.

All three samples were tested on a conductive base material consisting of a carbon filled polymeric film with a surface resistance of ~100 ohms/square, using the experimental product designated EXV-215, 90 PFW (as sold by FLEXcon Company, Inc. of Spencer, Mass.). The samples were tested using a QuadTech LCR Model 1900 testing device as sold by QuadTech, Inc. of Marlborough, Mass.

In particular, all three samples were then tested as per AAMI EC12-2000-4.2.2.1 (modified) and AAMI EC12-2000-4.2.2.4. The AAMI EC12-2000-4.2.2.1 test has an upper limit of 3000 Ohms for the face to face double adhesive part of the test, for a single point and a max average (12 test samples) of 2000 Ohms.

The AAMI EC12-2000-4.2.2.4 calls for retaining less than 100 mV in 5 sec after a 200 DC volt charge, again using a face to double adhesive layer.

Note the Table 1 below, which shows impedance (EC 12-2000-4.2.2.1) tested first; DOR (EC 12-2000-4.2.2.4) was run next on the same samples.

TABLE 1

| Sample | EC12-2000-4.2.2.1 (20 Hz) | EC12-2000-4.2.2.4 |
|---|---|---|
| Sample 1 | 60K Ohms (fail) | 0.0 volts in less than 5 sec. (pass |
| Sample 2 | 80K Ohms (fail) | 150 volts after 5 sec. (fail) |
| Sample 3 | 40M Ohms (fail) | 0.0 volts in less than 5 sec. (pass) |

Example 2

To determine the signal receptivity of this invention, the samples prepared for Example 1 were tested in accordance to the procedure outlined below. The samples used in testing as per AAMI EC12-2000-4.2.2.1 were used connected in series to a Wave Fowl Generator (Hewlett Packard 33120A 15 MHz Function/Arbitrary Waveform Generator) and in series an Oscilloscope (BK Precision 100 MHz Oscilloscope 2190), schematically shown below. Samples were tested at 3, 10 and 100 Hz; results are given below in Table 2 in % of transmitted signal received.

TABLE 2

|  | Sample 1 | Sample 2 | Sample 3 |
| --- | --- | --- | --- |
| 3 Hz | 95+% | 95% | No signal |
| 10 Hz | 95+% | 95% | No signal |
| 100 Hz | 95+% | 95% | No signal |

Example 3

Samples that passed the DOR test (AAMI EC12-2000-4.2.2.4) were retested for impedance as per AAMI EC12-2000-4.2.2.1 (modified), upon rechecking, samples 1 & 3 had a remarkable change. Samples 1 and 3 now had an impedance of less than 1K Ohms. In sample 2, the signal receptive medium was unchanged post DOR test; only those samples with the dispersed conductive particles changed. Further, the resulting lower impedance was still anisotropic, i.e., in the Z direction (noting Example 4 as to how the anisotropic property was determined). In addition the parallel capacitance (CP) of the post DOR material actually increases as the Z impedance decreases, as shown below in Table 3.

TABLE 3

|  | Ohms (Z direction) | CP Farads | DC Resistance Ohms |
| --- | --- | --- | --- |
| Sample 1 pre-DOR | 60K | 11.0 nF | 80K |
| Sample 1 post-DOR | 860 | 61.6 nF | 790 |
| Sample 3 pre-DOR | 13M | 0.06 nF | 100+M |
| Sample 3 post-DOR | 1.9K | 41.2 nF | 1.45K |

Example 4

The anisotropic property was validated by the following test procedure. Signals at 3, 10, 100, Hz were generated, and fed to a first copper shunt, which was placed on the conductive adhesive. A second copper shunt was placed on the same conductive adhesive ~0.004" (100 microns) apart from the first shunt, which was connected (in series) to an oscilloscope. The base substrate was a dielectric material (PET film). Following electrophoresis therefore, the composite may have a resistance of less than about 3,000 Ohms, less than about 2,000 Ohms, less than about 1,000 Ohms or even less than about 500 Ohms.

If the Sample 1 adhesive was isotropic it would have been expected to pick up a signal on the oscilloscope. If the Sample 1 adhesive was anisotropic it would have been expected that no signal would be received on the oscilloscope. The result was that no signal was detected.

Figure 10A:
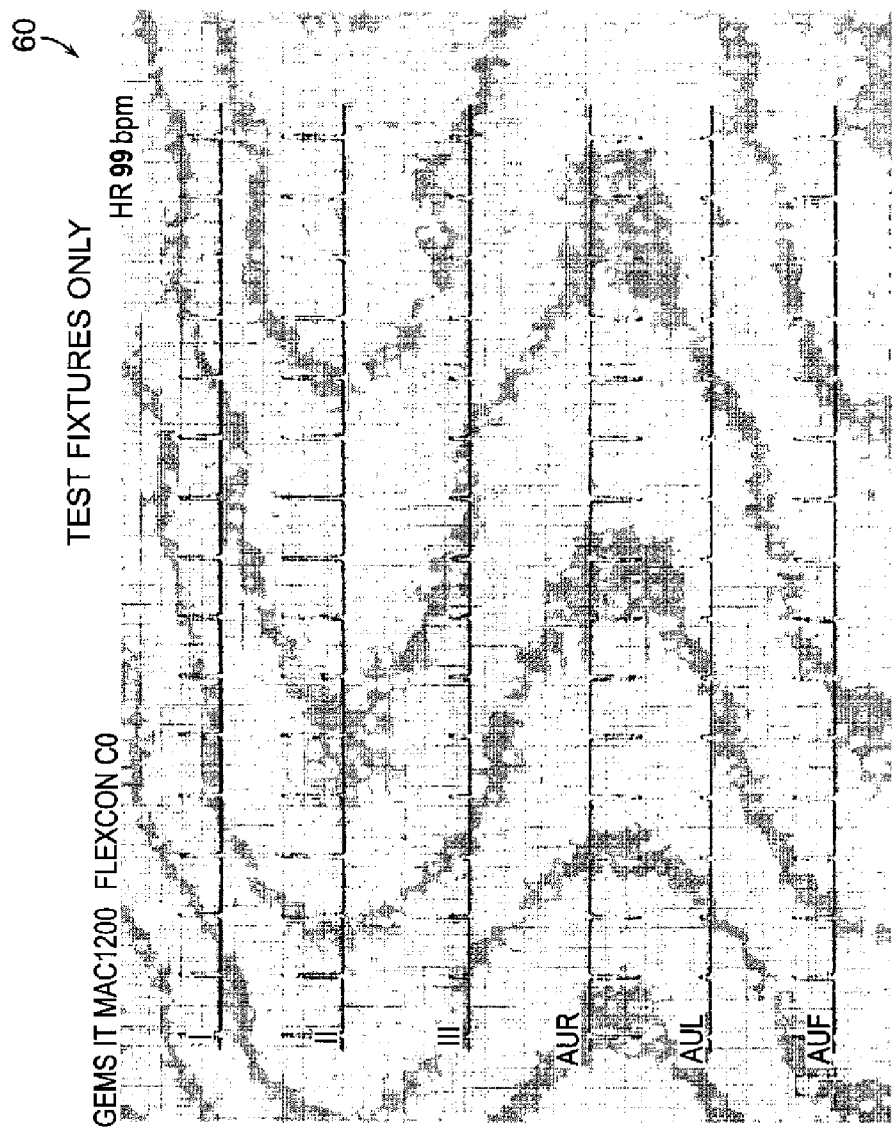
FIGS. 10A and 10B show illustrative graphical representations of biomedical sensor output date in a conventional anisotropic measurement device, and in unitary a composite in accordance with an embodiment of the invention respectively.
Figure 10B:
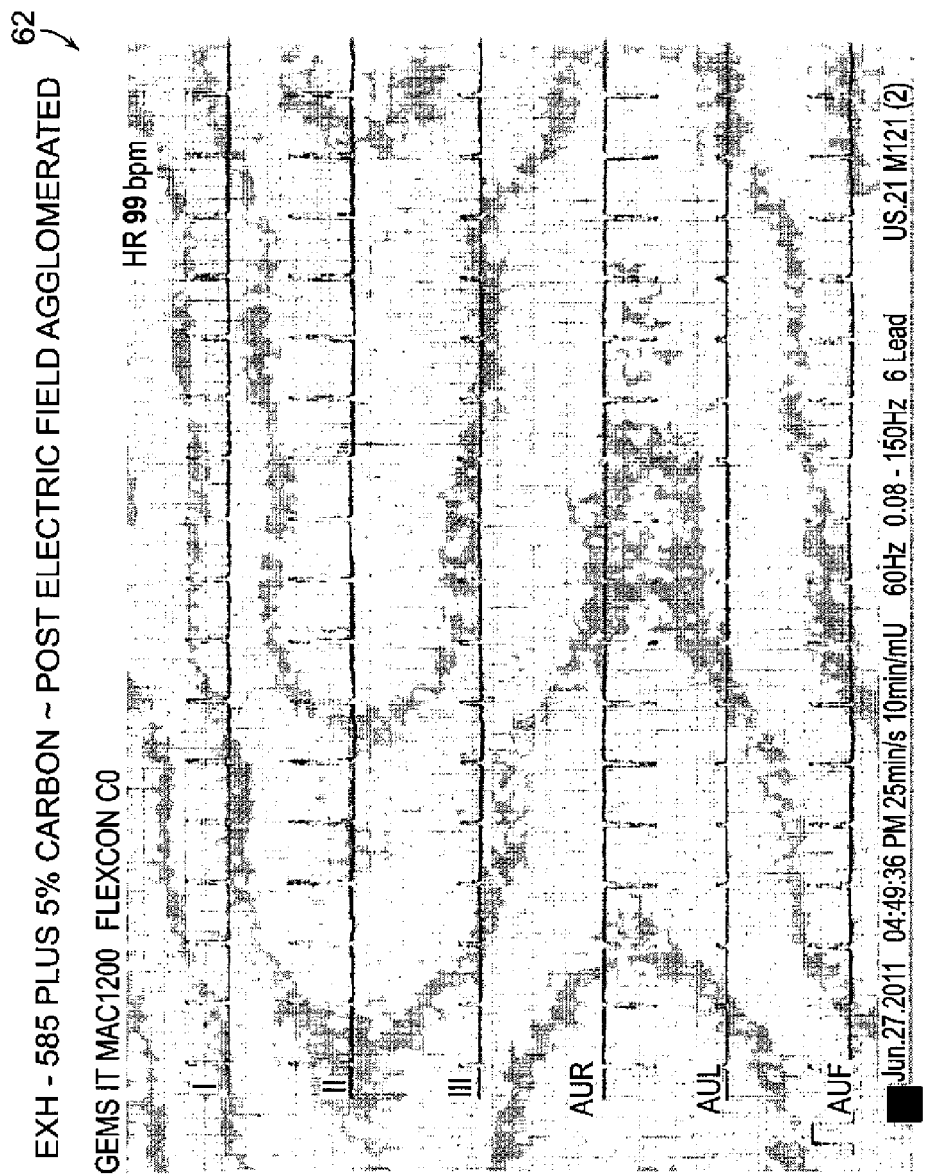

FIG. 10A shows at 60 a set of ECG test recordings using conventional biomedical sensors, and FIG. 10B shows at 62 the same set of ECG signals recorded using a biomedical sensor in accordance with an embodiment of the invention.

The electrophoresis result does not appear to rely on the presence of the polar material in the composite. It is believed that the carbon particles are agglomerated by the electric field applied during the DOR test; that the electric field generated by the 200 DC volts being applied across the conductive particle containing SRM and/or the conductive particles just with a PSA (no polar organo-salt), is sufficient to cause the particles to agglomerate together.

Figure 11:
FIGS. 11 and 12 show illustrative micro-photographic views of composites of the invention at different magnifications.

The agglomerated structures spanning from one electrode to the other are the reason an anisotropic conductive PSA is formed. To examine these agglomerations, reference is made to FIG. 11, which shows at 70 an in situ formed conductive structure as per this invention. In particular, FIG. 11 shows a 10× view looking down from the top of a conductive structure. The dark areas are the agglomerated particles the lighter area represents particle poor areas, i.e., places from which particles migrated.

Figure 12:
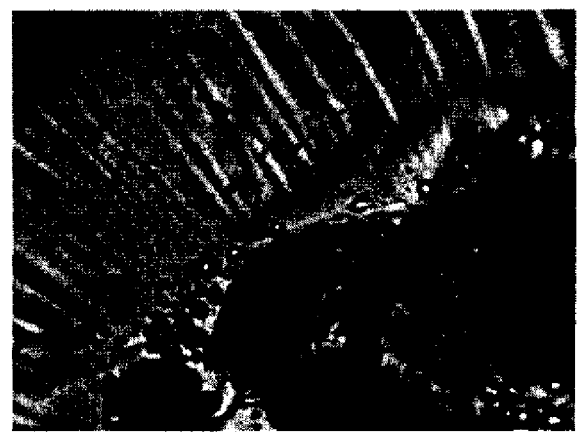

This particle migration effect can be shown in more detail by looking at FIG. 12, which shows at 72 a 100× magnification of a conductive structure, again looking down from the top but focused more towards the edge, showing the lighter, particle poor areas. The clear material is the continuous medium, in this case a PSA, FLEXcon's V-95 acrylic adhesive. Note the striations or grooves in the clear V-95, and also note that the few particles remaining are aligned with the striations. The starting material was a uniform particle distribution in continuous medium, thus under the electric field generated by the DOR test, the particles move together to form the conductive structure. Again, this agglomeration phenomenon may be referred to as electrophoretic or in the case of an AC electric field, dielectrophoretic effect, both of which are referred to herein as an electrophoresis process.

It is significant, however, that in this case the agglomeration occurs in a non-aqueous high viscosity medium. In accordance with the present invention, the continuous medium is a dielectric and is in full contact with the conductive particles (at the particle loading levels) and the medium is a viscoelastic liquid, i.e., has a very high viscosity, five times plus orders of magnitude higher (as measured in centipoises) than water dispersions (often measured in the only the 10 s of centipoises).

Again, what is postulated here is that, as in the case of particle agglomeration via an overcharge electric field in an aqueous continuous medium, a slight charge is induced on a nearby particle near an electrode. With the continuous medium being less polar and more dielectric than water however, a greater charge build-up can occur on a particle in the electric field.

With water as the continuous medium the higher polarity would mitigate the charge build up, further if the applied electric field were increased (higher voltage) electrolysis of the water would become a competing complication. With a PSA (FLEXcon's V-95 acrylic adhesive) as the continuous medium there is much less charge mitigation and no substantial electro-chemical process that occurs.

This charge build-up on the particle increases the attractive forces between the particle and the electrode, thus drawing the particle to the electrode in spite of the higher viscosity of the continuous medium. Further, the first particle that reaches the electrode forms an incremental high spot on said electrode thus the electric field is moved closer to the other electrode, as more particles join the agglomeration the field strength increase as the distance to the opposite electrode decreases, thus accelerating the agglomeration growth.

The DOR test involves a plane to plane electrode arrangement; after a few conductive structures are formed therefore, the electric field between the two electrodes is mostly dissipated due to the contacts already made between the electrodes. Thus the first structure will form, where there is one spot where the two planes are closer to one another or there is an uneven distribution of carbon such that a slightly higher density of the conductive particles are at one increment, between the plane, in other words that point of least resistance.

As a result using the plane to plane method in forming these structures has some limits as to the position and number of conductive structures formed. When a point-to-plane or point-to-point method is used to introduce the electric field however, more discrete in position and number of conductive structures would be formed as each point has its own electric field which is not readily dissipated when nearby conductive structures are fanned.

This was demonstrated by using a lab corona treating device on a conductive substrate that was grounded. The lab corona treating device acted like a series of point sources to a plane receiving substrate. What resulted was a uniformly distributed conductive structure across the surface of the adhesive.

The testing of the stability of the in situ formed electrically conductive structures was accomplished by placing post DOR test samples in an oven at 160° F. (71° C.) for 16 hours and retesting the impedance (AAMI EC12-2000-4.2.2.1.) and signal receptive properties. In all cases the samples maintained the lower impedance.

The invention therefore provides that an overload protected capacitively coupled, water content insensitive, composite may be provided that includes a polymer and a polar material dispersed therein, and electrically conductive particles, such that in the event of overcharging, the impedance as measured by AAMI EC12-2000-4.2.2.1 becomes less than 3,000 Ohms. The conductive particles may be in the form of carbon, and may be provided in a concentration greater than 1% on solids, dry weight. The composite may be anisotropic, and the polymer may be a pressure sensitive adhesive for use in an ECG electrode that satisfies the standards of AAMI EC-12-2000-422.4 for overload recovery.

Figure 13:
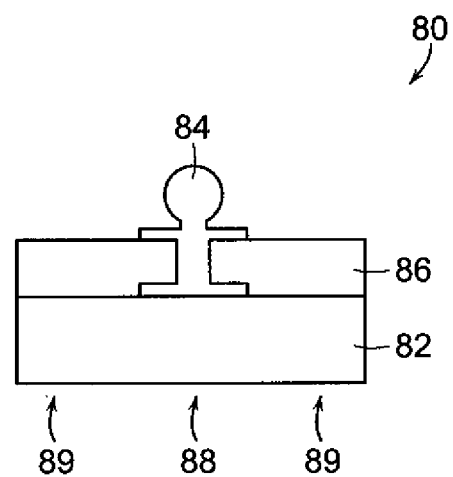
FIGS. 13-16 show illustrative diagrammatic views of biomedical electrodes in accordance with various embodiments of the invention.

FIG. 13 shows a biomedical electrode 80 in accordance with an embodiment of the invention that includes a composite 82 of the invention including a polymer, a polar material as discussed above, and conductive particles. Biomedical signals from the underside of the electrode (as shown at 88) may be picked up by, for example, a snap connector 84 that is potted within a further supporting material 86 such as another polymeric material. Note that bioelectric signals that are not directly under the snap connector (as shown at 89) are not picked up by the snap connector 84.

Figure 14:
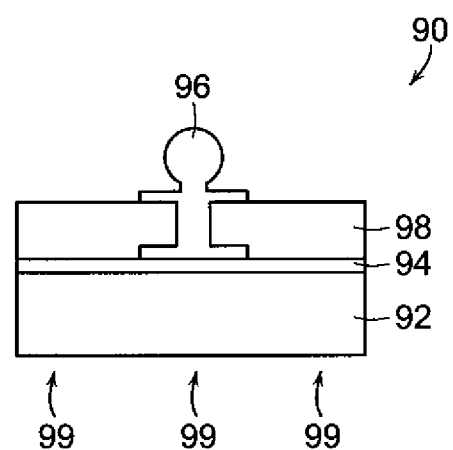

FIG. 14 shows a biomedical electrode 90 in accordance with another embodiment of the invention that includes a composite 92 of the invention again, including a polymer, a polar material as discussed above, and conductive particles. A conductive layer 94 is formed on one side of the composite 92 to provide that biomedical signals from the entire underside of the electrode (as shown at 99) may be picked up by, for example, a snap connector 96 that is potted within a further polymeric material 98 as discussed above.

The use of the composite 92 of the present invention, however, provides that the conductive layer 94 does not need to be formed of an expensive material such as silver/silver chloride (Ag/AgCl) as is required with hydrogels. Hydrogels require such specialized conductive layers because the ionic conductivity of the hydrogel must ionically couple to the electrode. In accordance with the present invention on the other hand, the conductive layer 94 may be fanned of an inexpensive deposited layer (e.g., vacuum deposited or sputter coated) of, for example, conductive particles such as those discussed above but in a much higher concentration to form a conductive layer upon deposition. Such less expensive materials may be used for the conductive layer because the mechanism for conduction (whether by the polar material or the conductive material) is not ionic conductivity.

Figure 15:
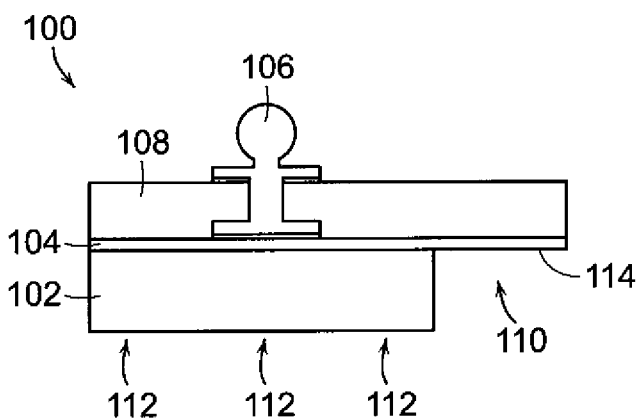

The use of inexpensive materials for the conductive layer also permits that a variety of connection options may be provided on a single biomedical electrode. For example, FIG. 15 shows a biomedical electrode 100 in accordance with another embodiment that includes a composite 102 of the invention again, including a polymer, polar material as discussed above, and conductive particles. An extended conductive layer 104 is formed on one side of the composite 102 to provide that biomedical signals from the entire underside of the electrode (as shown at 112) may be picked up by, for example, a snap connector 106 that is potted within a further polymeric material 108 as discussed above and/or a tab connector 110 having an exposed portion 114 of the conductive layer 104.

Figure 16:
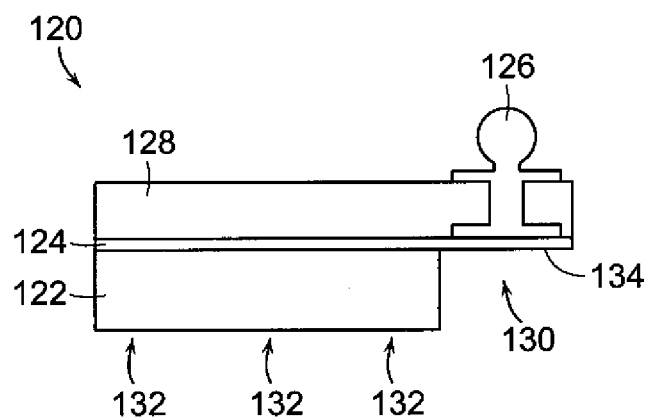

FIG. 16 shows a biomedical electrode 120 in accordance with another embodiment that includes a composite 122 of the invention again, including a polymer, polar material as discussed above, and conductive particles. An extended conductive layer 124 is formed on one side of the composite 122 to provide that biomedical signals from the entire underside of the electrode (as shown at 132) may be picked up by, for example, a snap connector 126 that is potted within a further polymeric material 128 as discussed above and/or a tab connector 130 having an exposed portion 134 of the conductive layer 124.

Figure 17:
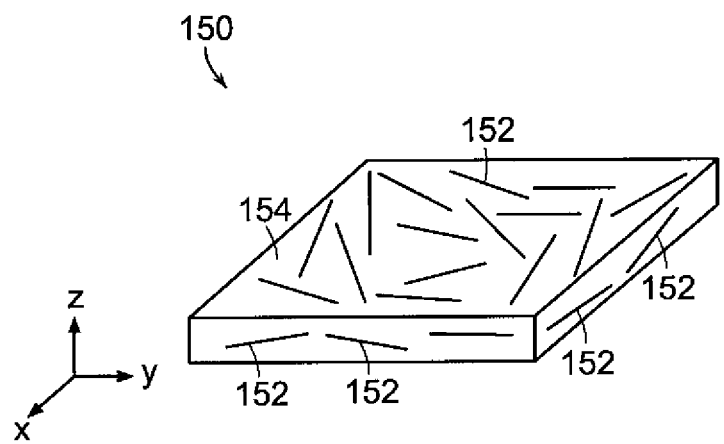
FIGS. 17-18 show illustrative diagrammatic views of composites of a further embodiment of the invention employing carbon nanotubes before and after electrophoresis.
Figure 18:
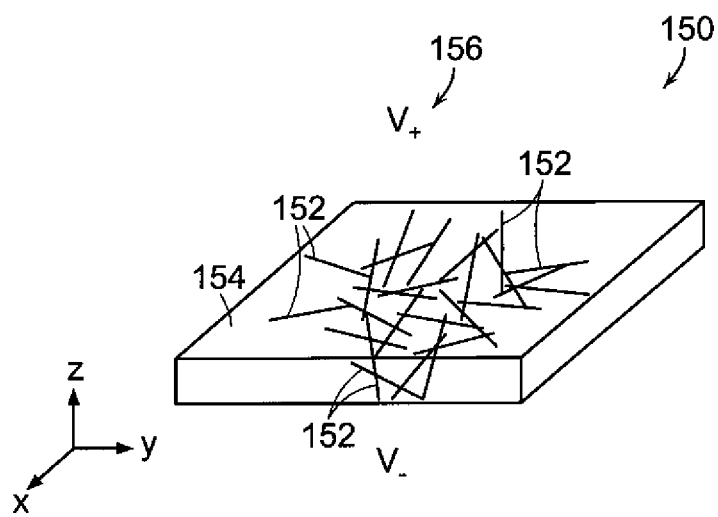

Composites of further embodiments of the invention may employ carbon nanotubes. Such composites also undergo the electrophoresis process discussed above during overcharging, but the agglomeration results in a jumbled nest of the nanotubes given the very high aspect ratio of the nanotubes (e.g., upwards of 1000 to 1). For example, a composite 150 may include carbon nanotubes 152 dispersed within a binder material 154 as shown in FIG. 17. In the presence of an electric field that is applied in the Z direction (as shown at 156 in FIG. 18), the particles agglomerate but because the particles are so long, they become entangled with one another when agglomeration occurs. This results in the particles not only providing electrical conductivity in the Z direction, but also providing electrical conductivity in the X and Y directions as well due to the entangled mass of particles extending in the X and Y directions as well as the Z direction as shown in FIG. 18.

Example 5

In accordance with a further example therefore, an adhesive mixture including FLEXcon's V-95 acrylic adhesive, a polar material (Arquad HTL-8 sold by AkzoNobel, 20% solids on solids of the V-95 adhesive, and 0.04% single walled semi-conductive carbon nanotubes (CNTs). The mixture was provided in a 3% solids paste in a 72/28 solvent blend isopropyl alcohol/n-butyl alcohol (sold by Southwest Nanotechnologies of 2501 Technology Place, Norman, Okla. The mixture was sonicated for 30 minutes to evenly disperse the CNTs throughout the adhesive/arquad premixture.

The mixture was then coated, dried and cured as discussed above to a 2 mil (50 micron) dried thickness. The adhesive composites were made and tested as discussed above. The results were that the pre-DOR test (as per EC12-2000-4.2.2.1) showed an impedance of 100 k Ohms. The DOR test (as per EC12-2000-4.2.2.4) was pass, and that the impedance post EC12-2000-4.2.2.1 was 5 K Ohms. The signal receptivity was tested as in Example 1 to be both 95% before and after DOR. The anisotropy test as discussed above with respect to Example 3, found that there was an X and Y conductivity component to the composite post DOR. It is expected that more uniform istropic conductive coatings may be formed.

Example 6

As noted above, if the particle concentration in a pressure sensitive adhesive is high enough to form a network in which particle-to-particle contact is maintained then there is little chance that the adhesive component is present in high enough concentrations to flow out to make surface-to-surface contact between the substrates and an electrode, i.e., act as an adhesive. In a further example, to the adhesive material of Sample 1 (the V-95 PSA and polar material) was added 25% by weight of the carbon particles of Sample 1. The composite was then coated and dried onto a polyester based siliconized release liner to a 2 mil (50 micron) dry deposition. The resulting coating had substantially no measurable PSA properties (tack, peel, shear). An electrically conductive network, however, had formed in the composite, and this composite was found to have a DC resistance of about 100 Ohms both before and after electrophoresis.

Those skilled in the art will appreciate that numerous modifications and variations may be made to the above disclosed embodiments without departing from the spirit and scope of the present invention.

What is claimed is:

1. An alternating electric field responsive biomedical composite providing capacitive coupling through the composite, said biomedical composite comprising a binder material, a polar material that is substantially dispersed within said binder material, and electrically conductive particles within the binder material, wherein said polar material is responsive to the presence of an alternating electric field, and wherein said electrically conductive particles are not of sufficient concentration to form a conductive network through the composite.

2. The composite of claim 1, wherein said binder material includes a polymeric material.

3. The composite of claim 1, wherein said electrically conductive particles include any of carbon powder, flakes, granules or nanotubes.

4. The composite of claim 3, wherein the carbon is in the form of graphite.

5. The composite of claim 1, wherein said electrically conductive particles have densities within the range of about 0.35 g/cm$^3$ and about 1.20 g/cm$^3$.

6. The composite of claim 1, wherein said electrically conductive particles have densities within the range of about 0.5 g/cm$^3$ and about 1.0 g/cm$^3$.

7. The composite of claim 1, wherein a surface energy of the conductive particles is higher than a surface energy of the binder material.

8. The composite of claim 1, wherein the conductive particles are randomly distributed within the composite.

9. The composite of claim 1, wherein the conductive particles are provided in the composite in an ordered arrangement.

10. The composite of claim 1, wherein the composite includes a conductive layer that is formed of carbon.

11. The composite of claim 1, wherein the composite includes a conductive layer having no silver/silver chloride.

12. The composite of claim 11, wherein the composite includes a plurality of connection types for electronically coupling to monitoring equipment.

13. An alternating electric field responsive composite providing capacitive coupling through the composite for biomedical applications, said composite comprising a binder material, a polar material that is substantially dispersed within said binder material, and electrically conductive particles within the binder material, wherein said binder material and said polar material exhibit mutual molecular compatibility, and wherein said electrically conductive particles remain substantially isolated from one another within the binder material.

14. The composite of claim 13, wherein said electrically conductive particles include any of carbon powder, flakes, graphite granules or nanotubes.

15. The composite of claim 13, wherein said electrically conductive particles have densities within the range of about 0.5 g/cm$^3$ and about 1.0 g/cm$^3$.

16. The composite of claim 13, wherein a surface energy of the conductive particles is higher than a surface energy of the binder material.

17. A method of providing a overcharge protection in an alternating electric field responsive composite, said method comprising the steps of providing a binder material, adding a polar material to the binder material such that the polar material becomes substantially dispersed within said binder material and the binder material and the polar material exhibit mutual molecular compatibility, and adding electrically conductive particles to the binder material such that the electrically conductive particles remain substantially isolated from one another within the binder material unless and until an overcharge is applied that causes the electrically conductive particles to undergo electrophoresis within the composite and form conductive paths through the composite.

18. The method of claim 17, wherein said electrically conductive particles have densities within the range of about 0.5 g/cm$^3$ and about 1.0 g/cm$^3$.

19. The method of claim 17, wherein a surface energy of the conductive particles is higher than a surface energy of the binder material.

* * * * *

UNITED STATES PATENT AND TRADEMARK OFFICE
CERTIFICATE OF CORRECTION

PATENT NO. : 8,673,184 B2
APPLICATION NO. : 13/272545
DATED : March 18, 2014
INVENTOR(S) : Kenneth Burnham et al.

Page 1 of 1

It is certified that error appears in the above-identified patent and that said Letters Patent is hereby corrected as shown below:

In the Specifications:

In Column 11, line 20 delete "fanned" and replace with --formed--.

In Column 12, line 4 delete "fanned" and replace with --formed--.

Signed and Sealed this
Twentieth Day of May, 2014

Michelle K. Lee
*Deputy Director of the United States Patent and Trademark Office*